United States Patent
Bathelt et al.

(10) Patent No.: US 10,799,886 B2
(45) Date of Patent: Oct. 13, 2020

(54) METHOD FOR THERMALLY DISINFECTING A CENTRIFUGE

(71) Applicant: GEA MECHANICAL EQUIPMENT GMBH, Oelde (DE)

(72) Inventors: Thomas Bathelt, Oelde (DE); Dirk Esseling, Oelde (DE)

(73) Assignee: GEA MECHANICAL EQUIPMENT GMBH, Oelde (DE)

( * ) Notice: Subject to any disclaimer, the term of this patent is extended or adjusted under 35 U.S.C. 154(b) by 147 days.

(21) Appl. No.: 16/098,585

(22) PCT Filed: May 4, 2017

(86) PCT No.: PCT/EP2017/060715
§ 371 (c)(1),
(2) Date: Nov. 2, 2018

(87) PCT Pub. No.: WO2017/198475
PCT Pub. Date: Nov. 23, 2017

(65) Prior Publication Data
US 2019/0143343 A1 May 16, 2019

(30) Foreign Application Priority Data
May 18, 2016 (DE) .......................... 10 2016 109 086

(51) Int. Cl.
*A61L 2/07* (2006.01)
*B04B 15/06* (2006.01)
*B04B 1/08* (2006.01)

(52) U.S. Cl.
CPC ............... *B04B 15/06* (2013.01); *A61L 2/07* (2013.01); *B04B 1/08* (2013.01)

(58) Field of Classification Search
CPC ........................................................ A61L 2/07
See application file for complete search history.

(56) References Cited

U.S. PATENT DOCUMENTS

| 3,476,310 | A | 11/1969 | Poppenberg |
| 3,598,304 | A | 8/1971 | Hemfort |
| 4,263,258 | A * | 4/1981 | Kalasek ............... A61L 2/24 |
| | | | 422/113 |
| 2011/0195832 | A1* | 8/2011 | Rudman ............. B21D 22/22 |
| | | | 494/73 |

(Continued)

FOREIGN PATENT DOCUMENTS

| DE | 1910211 A1 | 9/1970 |
| DE | 2656271 A1 | 7/1977 |

(Continued)

OTHER PUBLICATIONS

International Search Report dated Aug. 8, 2017 in related International Application No. PCT/EP2017/060715.

(Continued)

*Primary Examiner* — Donald R Spamer
(74) *Attorney, Agent, or Firm* — Patent Portfolio Builders PLLC

(57) ABSTRACT

A method for thermally disinfecting a centrifuge to reduce the quantity of germs therein, the centrifuge having a rotatable drum and being used for centrifugally processing a product, involves reducing the quantity of germs using vapor that is not pressurized or which is at atmospheric pressure.

16 Claims, 1 Drawing Sheet

(56) References Cited

U.S. PATENT DOCUMENTS

2012/0040816 A1    2/2012  Thorwid et al.
2013/0084225 A1*  4/2013  Buczynski ................ A61L 2/07
                                                                                       422/292

FOREIGN PATENT DOCUMENTS

| DE | 4108538 A1 | 9/1992 |
|----|------------|--------|
| GB | 1518239 A | 7/1978 |
| JP | 2007125450 A | 5/2007 |
| WO | 2004058173 A2 | 7/2004 |

OTHER PUBLICATIONS

Search Report dated Feb. 26, 2018 in related DE Application No. 10 2016 109 086.7.
Written Opinion dated Aug. 8, 2017 in related International Application No. PCT/EP2017/060715.

* cited by examiner

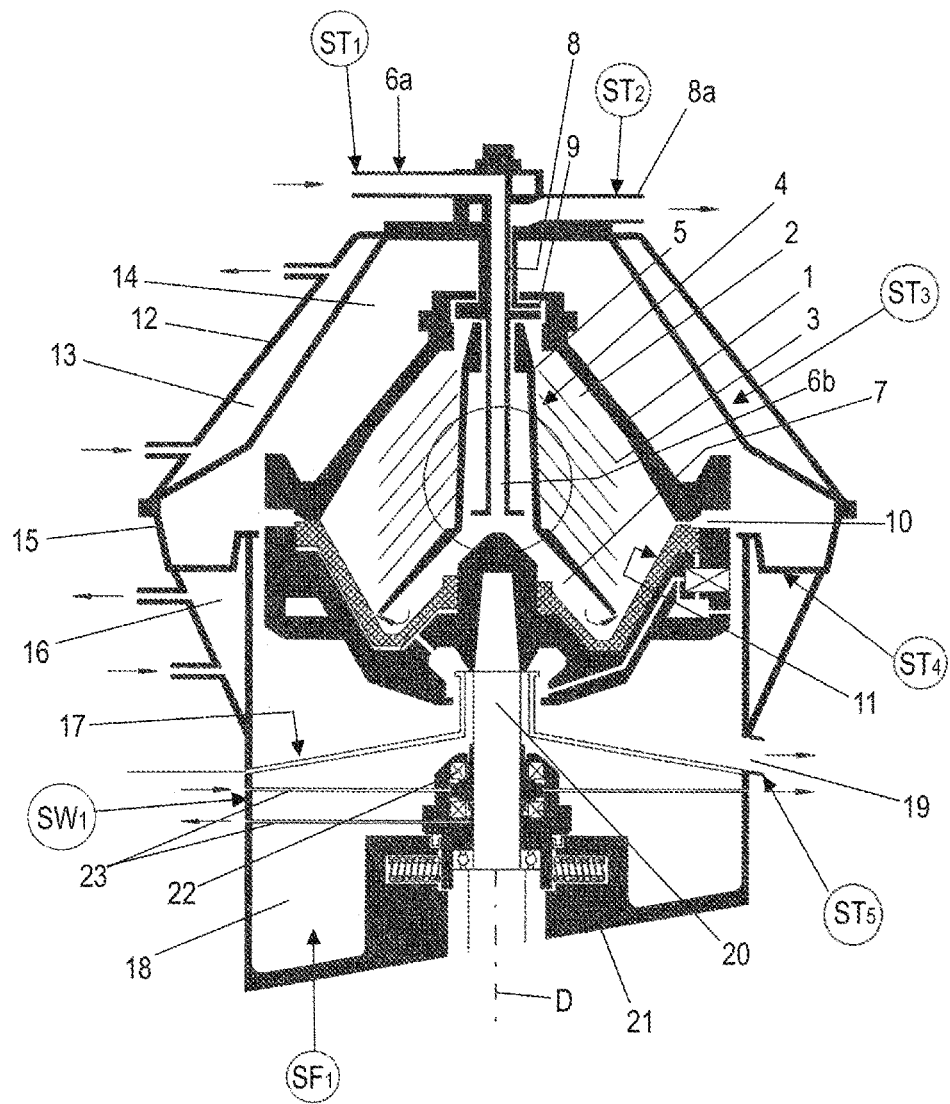

METHOD FOR THERMALLY DISINFECTING A CENTRIFUGE

BACKGROUND AND SUMMARY OF THE INVENTION

Exemplary embodiments of the invention relate to a method for thermally disinfecting a centrifuge—i.e., for reducing the quantity of germs on the surfaces of the flow paths, the centrifuge having a rotatable drum and being used for centrifugally processing a product.

In the centrifugal processing of certain products, i.e., in certain applications, it is necessary not only to clean the centrifuge—e.g., by means of a CIP process—but also to disinfect it in order to kill germs. Vapor sterilization is generally used for this purpose.

In vapor sterilization, hot steam under pressure is passed through the centrifuge. For this purpose, steam at a temperature of 121° C. or 134° C. is used in the case of centrifuges. The centrifuge is therefore supplied with steam under pressure. Vapor sterilization generally takes place at 127° C. and 2.5 bar.

Vapor sterilization with its high pressures gives rise to the necessity of using a "pressure vessel" (in the form of a drum and feed and discharge lines, among other elements), which meets the locally-applicable regulations. These regulations are usually the "ASME boiler and pressure vessel code" or the "Pressure Equipment Directive" (implemented according to German code of practice "AD Regelwerk"). This requires corresponding calculations, materials, verification etc., which significantly increase the costs of the separator.

Starting from this prior art, exemplary embodiments of the invention are directed to a simplified method for reducing the quantity of germs in separators.

According to embodiments, a method for thermally disinfecting centrifuges—i.e., for reducing the quantity of germs therein—the centrifuges being used for centrifugally processing a product, involves performing disinfection using vapor that is not pressurized or which is at atmospheric pressure—not during the actual processing of the product but as it were in a pause in processing.

One particular advantage of this method can be regarded as the fact that no pressure vessel is required, that is to say, in particular, the drum and the feed and discharge lines thereof and/or the hood and the solids trap need only be designed for operation under atmospheric pressure. The method is very simple if steam under atmospheric pressure is used as the vapor. A thermal disinfection process is carried out, in which the objects to be disinfected are heated to reduce the quantity of germs by supplying steam under atmospheric pressure. The germ count is thereby reduced to a defined extent.

The method according to the invention, together with the variants thereof, is particularly suitable for applications in the biotechnology/pharmacology sector, in which thermal sanitization/disinfection is sufficient to replace thermal sterilization. This means that it is only necessary to kill germs at temperatures that can be achieved at atmospheric pressure with the vapor used. In such applications, the invention eliminates the otherwise required pressure vessel configuration.

It is furthermore advantageous if the vapor under atmospheric pressure is passed via the (entire) product path of the centrifuge. The path which the product and the individual phases thereof take into, through, and out of the separator is referred to here and below as the product path. This thus includes the feed with the feed pipe, the distributor, the centrifuging chamber with the separating disk stack, the outlet with the skimmer disk and the outlet line as well as optionally (in the case of solids separation) the outlet openings and the hood interior with a solids trap.

In the context of this application, the term "sanitization" refers to unpressurized thermal disinfection, i.e., "reduction of the quantity of germs". In contrast, sterility is achieved with vapor sterilization. Consequently, the aim of the "sanitization" according to the invention is a reduction in the quantity of relevant germs and microorganisms (sufficient for the specific application).

The drum preferably rotates at a predetermined speed while the vapor is passed through. Passing the vapor through while the drum rotates ensures optimized distribution of the vapor, improved temperature control and sealing with respect to the transmission chamber (drive chamber). The speed of the drum is preferably lowered to the lowest possible value at which penetration of vapor into the drive region is still just prevented.

Measurement of the effectively achieved temperatures (T) at relevant measurement locations (e.g., feed, product outlet, condensate outlet, hood, trap) is possible in a simple manner using temperature sensors. These monitor how long and where in the flow path or at the surfaces of the flow path which temperature has been reached during sanitization. In addition, it is advantageous to detect the moisture content in the drive chamber using a humidity sensor and/or to detect the water content in a lubricant system using a detector for water detection in lubricating oil. If predetermined limits are reached or exceeded during thermal sanitization, a warning message is output and/or sanitization is stopped.

BRIEF DESCRIPTION OF THE DRAWING FIGURE

The invention is described in greater detail below by means of an illustrative embodiments with reference to the figures, where:

FIG. 1 shows a schematic illustration of a separator without illustrating a drive motor.

DETAILED DESCRIPTION

FIG. 1 shows a centrifuge, in this case a separator, which has a rotatable drum 1. Here, this drum 1 is of double-cone design.

The drum 1 has a vertical rotation axis D. Arranged in the conical or, in this case, even double-cone-shaped drum 1, in the drum interior (in this case likewise double-cone-shaped by way of example)—also referred to as the centrifuging chamber 2—is a separating disk stack 3 consisting of conical separating disks 4. The separating disks 4 are arranged on a distributor shaft 5 of a distributor. A feed 6a having a feed pipe 6b projecting into the drum is used to feed a product to be processed into distributor ducts 7 and out of said ducts into the centrifuging chamber 2.

In the centrifuging chamber 2, the product to be processed is cleared of solids and, where applicable, separation into two or more liquid phases of different densities optionally takes place.

To remove the at least one liquid phase, use is made of one or more outlets 8 for liquid phases, which can be provided with skimmer disks 9, for example, and which open into an outlet line 8a.

In contrast, the solids are expelled outward from the centrifuge drum 1 by circumferentially distributed, radially extending outlet openings 10, preferably in the region of the maximum radius/circumference of the centrifuge drum. According to one variant (not shown here), these outlet openings 10 are provided with nozzles in order to continuously expel the solids. Alternatively, the outlet openings 10 are assigned a discontinuously operating closure mechanism. This can have a fluid-actuated piston valve 11, which closes the outlet openings 10 in one position and opens them in another position, thus allowing solids to be discharged.

The drum 1 is surrounded by a hood 12. Here, this hood 12 is of double-walled construction in some sections, allowing a fluid to flow through it in this double-walled section 13.

A hood interior 14 is formed between the drum 1 and the hood 12, the interior having or forming, toward the bottom, a solids trap 15, which serves to collect solids expelled from the drum 1. Another double-walled section 16, through which a fluid can flow, is formed on the hood 12 below the solids trap 15. This fluid can be a coolant (during product processing). However, it can also be vapor for heating the hood for thermal disinfection in these regions.

Arranged below the drum 1 is a diaphragm 17, which separates the hood interior from a drive chamber 18. A frame outlet 19 is formed at the diaphragm 17.

The drum 1 can be rotated by means of a drive spindle 20. This drive spindle 20 is rotatably mounted by means of one or more spindle bearings 22 in a machine frame 21, in the drive chamber 18 below the drum 1. Here, the drum 1 is mounted on an upper end of the drive spindle 20. A lubricant system 23 is used to supply the spindle bearings 22 with lubricant.

Operating parameters can be measured at various locations using at least one or preferably a plurality of sensors. These sensors are connected to a control unit (not shown here) for controlling the operation of the separator and also sanitization. For this purpose, it has a computer program, which controls the progress of sanitization.

Here, the sensors comprise
one or more temperature sensors ST1 to STn,
one or more humidity sensors SF1 and/or
one or more sensors SW1 for detecting water in the lubricating oil of the lubricating system 23.

The path which the product and the individual phases thereof take through and out of the separator is referred to below as the product path. Thus, this includes the feed 6a with the feed pipe 6b, the distributor 7, the centrifuging chamber 2 with the separating disk stack 3, the outlet 8 with the skimmer disk 9, the outlet line 8a, the outlet openings 10, and the hood interior 14 with the solids trap 15.

By means of at least the one or preferably a plurality of temperature sensors ST1 to STn (in this case five by way of example), the temperature can be measured at various locations and/or in regions at surfaces of the product path of the separator. For this purpose, one or more temperature sensors ST1 to STn are preferably provided to measure the corresponding temperature at one or more of the following locations: at the feed 6a with the feed pipe 6b, at the frame outlet 19, at the outlet line 8a and/or at/in the hood interior 14 and/or at or in the solids trap 15.

Here, the humidity sensor SF1 is arranged in the drive chamber 18 in order to monitor the air humidity in the drive chamber/region 18.

The sensor SW1 for measuring or sensing water in the lubricating oil is assigned to the lubricant system 23 in order to determine a/the water content in the lubricating oil.

The separator and the drum 1 thereof is/are preferably designed for continuous operation—i.e., continuous and not batch wise processing of a product. During this processing, a product to be processed is separated into phases of different density. For example, a liquid can be clarified and/or separated into two liquid phases of different density. Moreover, it is also possible in this way to concentrate a solid phase as a valuable product from a starting material and to separate it from a lighter phase.

For cleaning, a CIP cleaning process can be carried out (cleaning in place), wherein the centrifuge is cleaned and flushed with liquids, e.g., acids, alkalis or water.

In order to carry out further-reaching inactivation of germs and spores, provision is furthermore made to pass vapor through the product path of the separator for disinfection, the vapor not being pressurized but being under atmospheric pressure.

This disinfection method is suitable primarily for applications in the biotechnology/pharmacology sector, in which thermal sanitization/disinfection is sufficient to replace thermal sterilization. Consequently, the aim of "sanitization" is a reduction in the quantity of relevant germs and microorganisms (sufficient for the specific application).

A number of required temperatures and times for such a reduction in the quantity of germs/inactivation are indicated in table 1 below.

TABLE 1

Heat resistance

| Resistance level | Organism/pathogen | Temperature (° C.) | Time (min) |
|---|---|---|---|
| I | pathogenic streptococci, listeria, polio viruses | 61.5 | 30 |
| II | most vegetative bacteria, yeasts, molds, all viruses apart from hepatitis B | 80 | 30 |
| III | hepatitis B viruses, most fungus spores | 100 | 5-30 |
| IV | Bacillus anthracis spores | 105 | 5 |
| V | Bacillus stearothermophilus spores | 121 | 15 |
| VI | prions | 132 | 60 |

According to the invention, a reduction in the quantity of germs—i.e., thermal sanitization—is carried out with vapor which is not pressurized or is under atmospheric pressure. This is sufficient, for example, to kill the germs at heat resistance levels I to III if sanitization is carried out at an atmospheric pressure of 1 bar.

Because unpressurized application of vapor is used to sanitize the centrifuge, no pressure vessel is required, i.e., the drum 1 and the inlet and outlet lines 6, 6a, 8, 8a thereof, the hood chamber 14 and the solids trap 15 have only to be designed for operation under atmospheric pressure.

The path which the product and the individual phases thereof take into, through and out of the separator is referred to below as the product path. This thus includes the feed 6 with the feed pipe 6a, the distributor, the centrifuging chamber 2 with the separating disk stack 3, the outlet 8 with the skimmer disk 9 and the outlet line 8a as well as optionally (in the case of solids separation) the outlet openings 10 and the hood interior 14 with the solids trap 15.

In order to carry out further-reaching inactivation of germs and spores, provision is made to pass vapor through the entire product path of the centrifuge or, in this case, of the separator, the vapor not being pressurized for this purpose but being under atmospheric pressure.

The vapor is preferably fed in through the feed, then through the rotor or centrifuging chamber 2 and then through the outlet and the outlet line, the hood chamber 14, the solids trap 15 and, where applicable, optionally a protective hood.

In this way, controlled sanitization of the entire region of the centrifuge which is in contact with the product can be accomplished.

Passing the vapor through while the drum 1 rotates ensures the improved distribution of the vapor, improved temperature control and sealing with respect to the transmission chamber (drive chamber).

It is advantageously possible to measure the effectively achieved temperatures (TE) at relevant measurement locations by means of sensors ST1 to STn. Thus, the method is carried out until a predetermined minimum temperature has been achieved for a predetermined time period at one, a plurality of or each of the temperature sensors ST1 to STn, in accordance with the germs to be killed. According to table 1, this temperature and this time are preferably more than 61.5° C. for more than 30 minutes, in particular more than 80° C. for more than 30 minutes.

It is advantageous to detect the moisture content in the drive chamber 18 using the humidity sensor SF1 and/or to detect the water content in the lubricating oil in a lubricant system 23 using the detector SW1.

If predetermined limits for the moisture content in the drive chamber or the water content in the lubricating oil are reached or exceeded during thermal sanitization, a warning message is output and/or sanitization is stopped.

Although the invention has been illustrated and described in detail by way of preferred embodiments, the invention is not limited by the examples disclosed, and other variations can be derived from these by the person skilled in the art without leaving the scope of the invention. It is therefore clear that there is a plurality of possible variations. It is also clear that embodiments stated by way of example are only really examples that are not to be seen as limiting the scope, application possibilities or configuration of the invention in any way. In fact, the preceding description and the description of the figures enable the person skilled in the art to implement the exemplary embodiments in concrete manner, wherein, with the knowledge of the disclosed inventive concept, the person skilled in the art is able to undertake various changes, for example, with regard to the functioning or arrangement of individual elements stated in an exemplary embodiment without leaving the scope of the invention, which is defined by the claims and their legal equivalents, such as further explanations in the description.

REFERENCE SIGNS drum 1
centrifuging chamber 2
separating disk stack 3
separating disk 4
distributor shaft 5
feed 6a
feed pipe 6b
distributor ducts 7
outlet 8
outlet line 8a
skimmer disks 9
outlet openings 10
piston valve 11
hood 12
double-walled section 13
hood interior 14
solids trap 15
double-walled section 16
diaphragm 17
drive chamber 18
frame outlet 19
drive spindle 20
machine frame 21
spindle bearing 22
lubricant system 23
temperature sensors ST1 to ST5
humidity sensors SF1
sensors SW1
rotation axis D

The invention claimed is:

1. A method for thermally disinfecting a centrifuge by reducing a quantity of germs in the centrifuge, the method comprising:
   reducing the quantity of gems in the centrifuge using vapor that is not pressurized or which is at atmospheric pressure,
   wherein the centrifuge has a rotatable drum and is configured to centrifugally processing a product,
   wherein the vapor is passed through a feed, distributor ducts, a centrifuging chamber, a separating disk stack, and an outlet of the centrifuge,
   wherein, while the vapor is passed through the centrifuge, the drum is rotated at a speed below an operating speed of the centrifuge during centrifugal processing of the product and which is set to a lowest possible value at which penetration of vapor into a drive chamber of the centrifuge is prevented, and
   wherein the method further comprises measuring air humidity in the drive chamber.

2. The method of claim 1, wherein the vapor is steam under atmospheric pressure.

3. The method of claim 1, wherein the vapor under atmospheric pressure is passed via a product path of the centrifuge.

4. The method of claim 1, wherein the drum is rotated as the vapor is passed through the centrifuge.

5. The method of claim 1, wherein the vapor is also passed through outlet openings, a hood, or a solids trap of the centrifuge.

6. The method of claim 1, further comprising:
   measuring, at one or more measurement locations, effectively achieved temperatures.

7. The method of claim 6, wherein the effectively achieved temperatures are measured at the one or more measurement locations by using one or more temperature sensors, wherein the measurement locations are
   an inlet of the centrifuge,
   an outlet line of the centrifuge,
   a frame outlet of the centrifuge,
   a hood of the centrifuge, or
   a solids trap of the centrifuge.

8. The method of claim 6, wherein the method is performed out until a predetermined minimum temperature has been achieved for a predetermined time period at one, a plurality of, or all of the temperature sensors.

9. A method for thermally disinfecting a centrifuge by reducing a quantity of germs in the centrifuge, the method comprising:
   reducing the quantity of gems in the centrifuge using vapor that is not pressurized or which is at atmospheric pressure,
   wherein the centrifuge has a rotatable drum and is configured to centrifugally processing a product, wherein the vapor is passed through a feed, distributor ducts, a centrifuging chamber, a separating disk stack, and an outlet of the centrifuge, wherein, while the vapor is passed through the centrifuge, the drum is rotated at a speed below an operating speed of the centrifuge during centrifugal processing of the product and which is set to a lowest possible value at which penetration of vapor into a drive chamber of the centrifuge is prevented, and wherein the method further comprises measuring water content in a lubricating oil in a lubricant system of the centrifuge.

10. The method of claim 9, wherein the vapor is steam under atmospheric pressure.

11. The method of claim 9, wherein the vapor under atmospheric pressure is passed via a product path of the centrifuge.

12. The method of claim 9, wherein the drum is rotated as the vapor is passed through the centrifuge.

13. The method of claim 9, wherein the vapor is also passed through outlet openings, a hood, or a solids trap of the centrifuge.

14. The method of claim 9, further comprising:
measuring, at one or more measurement locations, effectively achieved temperatures.

15. The method of claim 14, wherein the effectively achieved temperatures are measured at the one or more measurement locations by using one or more temperature sensors, wherein the measurement locations are
an inlet of the centrifuge,
an outlet line of the centrifuge,
a frame outlet of the centrifuge,
a hood of the centrifuge, or
a solids trap of the centrifuge.

16. The method of claim 14, wherein the method is performed out until a predetermined minimum temperature has been achieved for a predetermined time period at one, a plurality of, or all of the temperature sensors.

* * * * *